United States Patent [19]

Couderc et al.

[11] 4,082,775

[45] Apr. 4, 1978

[54] PREPARATION OF D, L-PANTOLACTONE

[75] Inventors: Pierre Couderc, Bethune; Serge Hilmoine, Aire sur la Lys, both of France

[73] Assignee: Societe Chimique des Charbonnages, Paris, France

[21] Appl. No.: 701,586

[22] Filed: Jul. 1, 1976

[30] Foreign Application Priority Data

Jul. 7, 1975 France ............................... 75 21270

[51] Int. Cl.$^2$ .......................................... C07D 307/32
[52] U.S. Cl. .................................................. 260/343.6
[58] Field of Search ...................................... 260/343.6

[56] References Cited

U.S. PATENT DOCUMENTS

| 2,328,000 | 8/1943 | Finkelstein | 260/344 |
|---|---|---|---|
| 2,852,530 | 9/1958 | Ford | 260/343.6 |
| 2,863,878 | 12/1958 | Lynn | 260/343.6 |

FOREIGN PATENT DOCUMENTS 40-8336   4/1965   Japan ............................... 260/343.6

OTHER PUBLICATIONS

Schmidt, et al., C.A. 79:18140m (1973).
Schmidt, et al., C.A. 80: 133230y (1974).
Ishiguro, C.A. 81:169151h (1974).
Yamamoto, C.A. 82:3820w (1975).
Ito, et al., C.A. 82:155390u (1975).

*Primary Examiner*—Richard L. Raymond

[57] ABSTRACT

The invention relates to a method for the synthesis of D, L-pantolactone by the reaction of (1) of hydroxypivaldehyde with hydrocyanic acid produced in situ followed by (2) hydrolysis of the cyanohydrin obtained. The pantolactone may then be separated from the reaction mixture. Each of the reactions (1) and (2) are conducted under closely controlled conditions of concentration, temperature, pH and time and, by virtue of these conditions, a yield exceeding 90% may be obtained.

2 Claims, No Drawings

PREPARATION OF D, L-PANTOLACTONE

The present invention relates to a method for the preparation of D, L pantolactone. It is known that pantolactone may be prepared by the action of hydrocyanic acid on hydroxypivaldehyde, then by acid hydrolysis of the cyanohydrin obtained. The reaction formula may be written as follows:

(a) obtaining the cyanohydrin

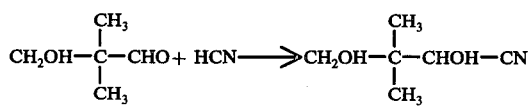

(b) hydrolysis in a highly acid medium (mineral acid HCl)

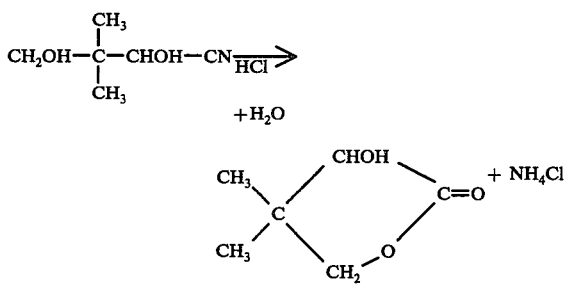

Hydrocyanic acid is produced within the reaction medium from hydrochloric acid and sodium cyanide (30% aqueous solution).

Two solvents are generally used during this synthesis; methanol for the preparation of the cyanohydrin then another solvent, which is generally chlorinated, for the extraction from the hydroorganic reaction medium, of the pantolactone formed.

Research workers who have described such a synthesis generally declare relatively low yields of final product, these yields are never greater than 85% and may be as low as 50%.

The applicant has undertaken research to see if it was possible to improve the yield of pantolactone from the successive reactions described above. Owing to certain particular and a priori unexpected precautions, the applicant was able to produce pantolactone with a yield equal to at least 90%.

The present invention therefore relates to a method for the synthesis of D, L pantolactone by the reaction of hydroxypivaldehyde on hydrocyanic acid produced in situ, then hydrolysis in a highly acid medium of the cyanohydrin obtained, characterised in that:

during this two-stage synthesis, a single solvent is used constituted by an alcohol having 5 or 6 carbon atoms.

the reaction (1) of hydroxypivaldehyde on hydrocyanic acid prepared in situ by the reaction of hydrochloric acid on an alkaline cyanide is carried out at a temperature of between 10 and 20° C, at a pH of between 8.2 and 9.2 adjusted by the addition of hydrochloric acid at the same time as the addition of alkaline cyanide, said additions being carried out over a period of between approximately 60 and approximately 70 minutes and corresponding to an excess of approximately 10% hydrocyanic acid with respect to the stoichiometry of the reaction.

and that the acid hydrolysis reaction (2) is carried out with an excess of concentrated hydrochloric acid, at a temperature of 100 to 105° C and for a duration of between 20 and 30 minutes, after which the pantolactone obtained is recovered.

According to the present invention, the use of a single solvent during the entire synthesis makes it possible to reduce losses and thus to increase the overall yield.

A solvent of this type should necessarily have the following properties:

be a solvent of the initial hydroxypivaldehyde, of the intermediate cyanohydrin and of pantolactone.

be slightly or non-miscible with water be chemically inert with regard to the reagents used (mainly HCN and HCl).

Surprisingly, the applicant discovered that alcohols having 5 or 6 carbon atoms comprised these properties and were suitable for carrying out the method according to the invention. From these alcohols, alcohols having 5 carbon atoms in particular may be used, such as neopentyl alcohol (2,2-dimethyl-1-propanol); 2-methyl-1-butanol, 1-pentanol, 3-pentanol and preferably isoamyl alcohol (3-methyl-1-butanol) still called isopentyl alcohol. This solvent also has the advantage of facilitating the azeotropic elimination of water contained in the reaction mixture after reaction (2) then the easy filtration of mineral salts contained in the organic solution thus obtained.

The purpose of controlling the operating conditions in the reaction (1) of hydroxypivaldehyde on hydrocyanic acid formed "in situ" is to prevent the formation of numerous secondary products such as neo-pentylglycol, neopentylglycol hydroxypivalate or dimethylhydracrylic acid.

The temperature of the reaction (1) should be between 10° and 20° C. For practical reasons, it may be wise to chose a temperature which may be controlled by cooling with running water and this is why it is preferred to operate at a temperature of approximately 18° C.

The pH should be between 8.2 and 9.2 throughout the entire reaction (1). This is why the reaction is preferably carried out by the slow and programmed introduction of alkaline cyanide (for example sodium cyanide) in a solution of hydroxypivaldehyde in an alcohol comprising 5 or 6 carbon atoms, continuous measurement of the pH and adjustment of this pH to the desired value by the addition of controlled quantities of hydrochloric acid in an aqueous solution (for example 37% by weight).

It should be arranged that the total quantity of hydrocyanic acid used corresponds to an excess of at least approximately 10% with respect to the stoichiometry of the reaction. The purpose of this excess is to prevent the presence of hydroxypivaldehyde which has not reacted during the hydrolysis reaction of the cyanohydrin.

At the end of this reaction (1) excess hydrochloric acid is added to bring the pH of the solution to approximately 3, a sufficient quantity of water is added to render all the mineral salts present soluble, then after separation of the aqueous phase from the organic phase, the latter is treated to hydrolise the cyanohydrin.

This acid hydrolysis (reaction 2) should also take place under very precise conditions. Firstly, the acid chosen should be concentrated hydrochloric acid (37% by weight). Then, it is necessary that the hydrolysis is carried out at a relatively high temperature, in order that it is rapid, but not too high, in order to prevent secondary reactions. This is why, according to the invention, it has been found that the temperature should be from 100 to 105° C and that this temperature should be maintained for a duration of between 20 and 30 minutes.

The solution obtained is then partly neutralised (to pH 4) by means of ammonia, then the pantolactone is purified.

The following non-limiting example illustrates the invention.

1200 parts by weight isoamyl alcohol and 260 parts by weight hydroxypivaldehyde are introduced into a sealed reactor provided with stirring, temperature control, measurement of the pH, two apparatus facilitating programmed introductions of the reagents, a reflux system comprising members for trapping the hydrocyanic acid and a nitrogen scavenger and this mixture is heated for several minutes at 40° to 45° C to obtain a homogeneous solution which is cooled to 15° C.

There is introduced into this solution:
449 parts by weight of a 30% aqueous solution of active sodium cyanide in a regular manner (i.e. in a constant manner in the course of time); the introduction lasts for 70 minutes;
a sufficient quantity of hydrochloric acid having a concentration of 37% by weight for maintaining the pH of the solution at 8.7;
throughout the introduction period, the temperature is maintained at 18° C.

After these reagents have been introduced, the reaction is allowed to continue for 20 minutes, at the same pH, whilst lowering the temperature to 13°–14° C, then hydrochloric acid is added in a sufficient quantity in order that the pH reaches 3. The total consumption of hydrochloric acid (having a concentration of 37%) rises to 290 parts by weight.

After these operations, 100 parts water are added and decantation takes place:
The following are formed:
an organic phase (1645 parts) whose composition is:
Alcohol — 72%
Water — 6.5%
HCN — 0.35%
Cyanohydrin — Approx. 20%
Sodium Chloride — Approx. 1.5%
and an aqueous phase (654 parts) whose composition is
Alcohol — 3%
Water — Approx. 75%
HCN — Approx. 0.15%
Sodium Chloride — Approx. 20%
Cyanohydrin — Approx. 1.5%

The organic phase (as described above) is separated and one adds, with stirring and at 20° C, 345 parts of hydrochloric acid having a concentration of 37% by weight. This addition is carried out over approximately 20 minutes.

The temperature of the mixture is then raised progressively to achieve boiling, which occurs at a temperature of the order of 103° to 104° C. The time taken to achieve this boiling is approximately 30 minutes. The medium is kept at boiling point for 30 minutes. The solution is then cooled to 20° C, then neutralised with 74 parts $NH_4OH$ having a specific gravity of 28° Baume.

The composition of the mixture obtained is as follows:
Pantolactone — 15.7%
Isoamyl alcohol — 57.5%
Water — 16.5%
$NH_4Cl$ — 9.1%
NaCl — 1.2%

The recovery of pure pantolactone from this mixture takes place by the following successive operations:
azeotropic distillation (water-isoamyl alcohol) at a pressure of the order of 10mm mercury, this distillation is stopped when the temperature at the head of the column reaches 41° C
the alcoholic solution of lactone still containing mineral salts is then filtered and the salts are washed with isoamyl alcohol.
the solution of pantolactone and isoamyl alcohol is then distilled continuously or discontinuously at reduced pressure (approximately 14mm mercury) one thus obtains on the one hand, alcohol which may be recycled and on the other hand raw pantolactone. The latter, which still contains some impurities, is subjected to rectification (also at a pressure of the order of 14mm mercury) to give a product having the following characteristics:
pantolactone — 98%
neopentylglycol — less than 0.1%
hydroxypivaldehyde — less than 0.1%
other secondary products approximately 1 to 1.5%.

The final yield with respect to hydroxypivaldehyde of the example given above is 92%.

The above-described method of preparation is repeated, but the important parameters are modified in order to show the influence of these parameters on the final yield of the process:
(a) the pH of the medium in which the preparation of cyanohydrin is carried out, is varied; this variation is produced by modifying the quantities of hydrochloric acid introduced;
The following results were obtained:

| pH | % Yield |
| --- | --- |
| 7 | 67 |
| 8 | 87 |
| 8.5 | 95 |
| 9 | 92 |
| 9.5 | 76 |
| 10 | 50 |

(b) with a pH of 9 and a temperature of 18° C, the introduction time for the reagents (sodium cyanide, thus hydrochloric acid to maintain the pH) in the manufacture of cyanohydrin were varied. The following results were obtained:

| Introduction time of the reagents in minutes | % Yield |
| --- | --- |
| 30 | 86 |
| 50 | 90 |
| 60 | 92 |
| 70 | 93 |
| 80 | 86 |
| 90 | 62 |

(c) the duration of hydrolysis is varied, i.e. the period during which the mixture of cyanohydrin and hydrochloric acid is kept at 103° C. In these tests, the duration of the rise in temperature was 30 minutes.

| Duration of hydrolydis in minutes | % yield |
| --- | --- |
| 5 | 87 |
| 10 | 93 |

-continued

| Duration of hydrolydis in minutes | % yield |
|---|---|
| 20 | 97 |
| 30 | 97 |
| 60 | 94 |
| 90 | 85 |

In the following claims, the scope of the invention is defined by a number of different parameters but it will be appreciated that this application also covers a process for producing pontolactone in which the parameters are varied between wide limits, outside those specified in the claims, if lower yields may be tolerated.

What is claimed is:

1. In a process for the preparation of D, L- pantolactone by the reaction of hydroxypivaldehyde with hydrocyanic acid produced in situ to yield cyanohydrin, subsequent hydrolysis in a high acid medium of the cyanohydrin to produce pantolactone and separation and purification of the pantolactone, the improvement comprising:

(a) using isoamyl alcohol as a single solvent during both reactions;
   (b) using a temperature of between 10 and 20° C and pH of 8.2 to 9.2 for the reaction of hydroxypivaldehyde with hydrocyanic acid produced in situ with the pH being adjusted within that range by the addition of hydrochloric acid at the same time as the addition of alkaline cyanide, said additions being carried out over a period of between approximately 60 and 70 minutes to provide an excess of approximately 10% hydrocyanic acid with respect to the stoichiometry of said reaction; and
   (c) the acid hydrolysis reaction being carried out with an excess of concentrated hydrochloric acid at a temperature of 100° to 105° C and for a period of between about 20 and 30 minutes.

2. Method according to claim 1, wherein separation and purification of the pantolactone comprises the azeotropic elimination of the water contained in the reaction mixture after reaction (2), then the filtration of the mineral salts contained in the organic solution thus obtained.

* * * * *